United States Patent [19]
Taenzer

[11] 4,434,799
[45] Mar. 6, 1984

[54] ULTRASOUND APPARATUS FOR MEDICAL EXAMINATIONS

[75] Inventor: Jon C. Taenzer, Palo Alto, Calif.

[73] Assignee: Siemens AG, Berlin & Munich, Fed. Rep. of Germany

[21] Appl. No.: 354,011

[22] Filed: Mar. 2, 1982

[51] Int. Cl.³ .............................................. A61B 10/00
[52] U.S. Cl. .................................................... 128/660
[58] Field of Search .................. 128/660; 73/618–620, 73/642, 644

[56] References Cited

U.S. PATENT DOCUMENTS

| | | | |
|---|---|---|---|
| 3,251,219 | 5/1966 | Hertz et al. | 128/660 X |
| 3,765,403 | 10/1973 | Brenden | 128/660 |
| 3,937,066 | 2/1976 | Green et al. | |
| 4,137,777 | 2/1979 | Haverl et al. | 128/660 X |
| 4,248,090 | 2/1981 | Glenn | 128/660 X |
| 4,274,421 | 6/1981 | Dory | 128/660 |

OTHER PUBLICATIONS

"Acoustical Holography", vol. 5, pp. 493–503, 1974.
"Acoustical Holography", vol. 6, pp. 1–13, 1976.

*Primary Examiner*—William G. Kamm
*Assistant Examiner*—Francis J. Jaworski
*Attorney, Agent, or Firm*—Karl F. Milde, Jr.

[57] ABSTRACT

The apparatus incorporates an ultrasonic wave-generating transducer for providing ultrasonic waves, a first and a second ultrasound window, a first guiding device for guiding the ultrasonic waves to the first window, an ultrasonic receiving transducer for transforming an acoustic image field received from the second window into electrical signals, and a second guiding device for guiding ultrasound transmitted through the second window to the receiving transducer. The ultrasound windows define an examination gap for insonifying a patient's organ positioned therein. The apparatus further incorporates a curved mirror for focusing the acoustic image field received from the gap onto the receiving transducer. The mirror is attached to a rocking device. Thus, the curved mirror is also used for scanning or sweeping the acoustic image field across the receiving transducer. Thus, an image of the object plane under examination is obtained. Preferably, the curved mirror may be filled with a substance having a low velocity of ultrasound as compared to the adjacent fluid medium contained in the second guiding device. This design eliminates the need for a large number of refractive and reflective surfaces, thereby reducing artifacts in the image.

22 Claims, 7 Drawing Figures

ULTRASOUND APPARATUS FOR MEDICAL EXAMINATIONS

CROSS REFERENCE TO RELATED APPLICATION

This application relates to the same technical field as the commonly owned application of Philip S. Green and Jon C. Taenzer, entitled "Compact Ultrasound Apparatus for Medical Examination", Ser. No. 284,930, filed on July 20, 1981. The content of this prior application is hereby incorporated herein by reference.

BACKGROUND OF THE INVENTION

1. Field of the Invention

This invention relates generally to an apparatus for generating an image according to an ultrasonic wave. In particular, this invention relates to an ultrasound apparatus for medical examinations of a patient. Still more particularly, this invention relates to an ultrasonic apparatus containing an ultrasonic wave-generating transducer for providing ultrasonic waves to insonify an object under observation, and an ultrasonic receiving transducer for converting at least a portion of an acoustic image field received from the object into electrical signals. The ultrasonic apparatus works in the transmission mode.

2. Description of the Prior Art

Ultrasonic systems of the type herein contemplated are disclosed, for instance, in U.S. Pat. No. 3,937,066, in *Acoustical Holography*, Vol. 5, pages 493-503, 1974, and in *Acoustical Holography*, Vol. 6, pages 1-13, 1976.

In the transmission mode C-scan ultrasonic systems according to the prior art, components such as the ultrasonic wave-generating transducer, the focusing lens, the scanning device, and the ultrasonic receiving transducer are arranged on the same axis. The prior art systems as a rule include as the scanning device a deflector assembly comprising a pair of acoustic prisms rotated in opposite rotational directions at the same speed. Due to the on-axis-arrangement, the whole system is usually very lengthy, and space problems may exist with respect to the placement in an examination room. Frequently a water tank is used between the emitting transducer and the receiving transducer. For examination purposes, the patient must enter the water tank. This is inconvenient especially for elderly patients. In addition, the prior art ultrasound systems generally do not provide for any clearance for non-observed organs of the patient. Therefore, in particular breast examinations are difficult to perform. Also, in a typical prior art ultrasonic system examinations of the breast in different directions are only possible if the patient herself moves into various positions. The system itself is stationary so that precise directional examinations are difficult to make.

SUMMARY OF THE INVENTION

1. Objects

It is an object of this invention to provide a compact ultrasound apparatus for examinations of an object, in particular for medical examinations of a patient.

It is another object of this invention to provide an ultrasonic apparatus for medical examinations of a patient who does not have to be immersed into a tank filled with a liquid such as water.

It is still another object of this invention to provide an ultrasonic apparatus for medical examinations of a patient which apparatus is provided with free space or clearances for parts or organs of the human body which are not under examination.

It is still another object of this invention to provide an ultrasonic apparatus for medical examinations of a patient which apparatus is adjustable to the thickness of the part under examination.

It is still another object of this invention to provide an apparatus particularly suitable for routine examinations of the female breast.

It is still another object of this invention to provide an ultrasound apparatus which can easily be used for examinations of a human organ such as the female breast in various directions.

It is still another object of this invention to provide an ultrasound apparatus working in the transmission mode which has only a comparatively small number of refractive surfaces, thus keeping the generation of reverberation artifacts small.

2. Summary

According to this invention, an ultrasound apparatus for medical examinations of a patient incorporates an ultrasonic wave-generating transducer for providing ultrasonic waves. The apparatus also incorporates a first and a second ultrasound window. A first guiding device containing a fluid medium is provided for guiding the ultrasonic waves from the transducer to the first window. The first and the second ultrasound windows define an examination space or gap for introducing therewithin and insonifying a portion of a patient's body. In the gap the ultrasound travels along a main insonification direction. The apparatus also incorporates an ultrasonic receiving transducer for converting at least a portion of an acoustic image field received from the examination gap into electric signals. A second guiding device also containing a fluid medium is provided for guiding the ultrasound which is transmitted through the gap from the second window to the ultrasound receiving transducer.

A mirror or mirror system is associated with the second guiding device. It is provided with a curved surface for focusing the acoustic waves passing through the gap at the ultrasonic receiving transducer. Thereby the aforementioned image field is formed. This image field generates an image of the patient's organ on the receiving transducer. The ultrasonic apparatus also contains an oscillating device for vibrating or rocking the mirror. The mirror thereby sweeps the acoustic image field across the receiving transducer.

Preferably an ellipsoidal mirror may be used. Its reflecting surface is a portion of an ellipsoid having a first and a second focus. The organ to be examined is positioned in the first focus, and the receiving transducer is positioned in the second focus.

The curved mirror may be filled with a substance of comparatively low ultrasound velocity. This substance may either be a liquid or a solid. This substance leads to two significant advantages. On the one hand, the amount of mechanical motion required for the deflection may be reduced with respect to a case where such a material is not present. On the other hand, the aberrations in the image can be kept smaller as compared to the case where such material is not present.

Since the acoustic axis of the apparatus is folded by the mirror, a compact construction is obtained. Since in general only a single mirror is required (and ultrasound lenses are not needed), the apparatus has only few refractive surfaces, thereby keeping the generation of artifacts low.

The foregoing and other objects, features and advantages of the invention will be apparent from the following more particular description of preferred embodiments of the invention, as illustrated in the accompanying drawings. Like elements are referred to by like reference numerals.

DETAILED DESCRIPTION OF THE PREFERRED EMBODIMENTS

Figure 1:
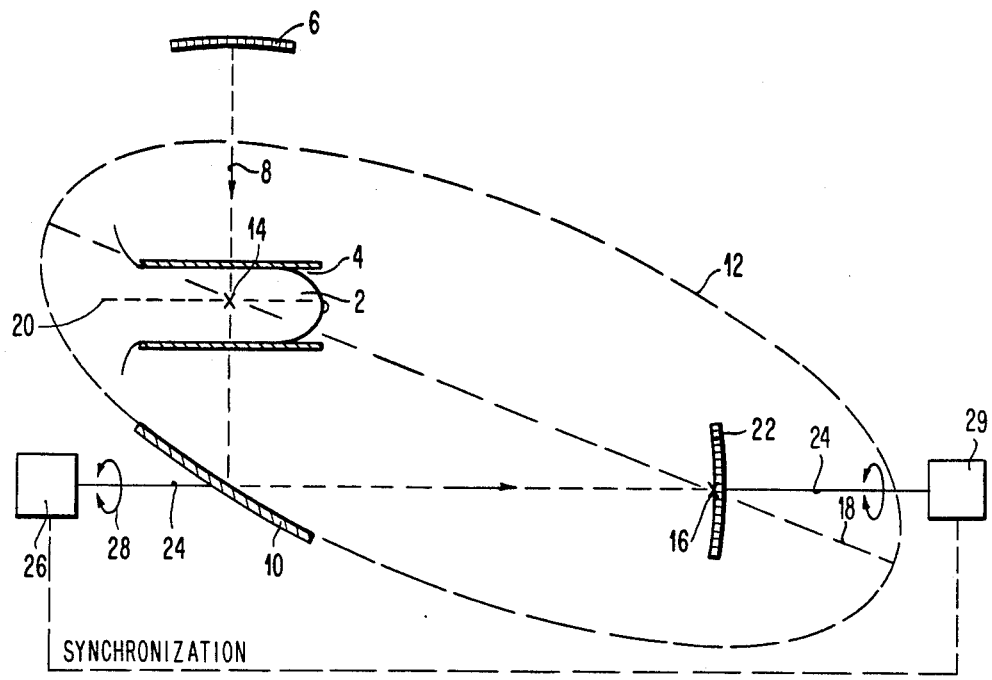
FIG. 1 is a schematic view of an ultrasonic transmission imaging system showing the principles of this invention.

In FIG. 1 an ultrasound imaging apparatus for examinations of an object 2 is schematically illustrated. The apparatus has the advantage that it requires only a few reflective and refractive surfaces thereby widely avoiding reverberation artifacts in the image of the object 2. In particular, the object 2 may be an organ of a patient such as the female breast. In an examination space 4, the organ 2 is slightly compressed so as to assume equal thickness.

An ultrasonic wave-generating transducer or source 6 generates ultrasonic waves which are transmitted to the object 2 under examination. The insonification direction is denoted by 8. The insonified object 2 passes on the received ultrasonic waves in accordance with its distribution of attenuation and scattering. The transmitted ultrasonic waves impinge on a concave ultrasonic reflector or mirror 10. The reflecting surface of the mirror 10 is ellipsoidal. That is, the surface of mirror 10 is a segment of an ellipsoid 12 having a first focus 14 and a second focus 16. The ellipsoid 12 is obtained by rotating an ellipse about its longitudinal axis 18 containing the foci 14 and 16. It will be noted that the first focus 14 is centered at the object plane 20 of the object 2 to be examined and that the second focus 16 is centered at an ultrasonic receiving transducer 22. This transducer is preferably an array of transducer elements, as is well-known in the art. The transducer 22 may be curved.

The mirror 10 is mechanically moved back and forth or rocked about an axis 24 by a suitable rocking device 26, as indicated by a double arrow 28. In the present embodiment, the axis 24 of rotation is arranged perpendicularly to the main insonification direction 8 and passing through the second focus 16. The receiver array 22 may additionally be rocked about the axis 24 and in synchrony with the mirror 10 to provide reduced image distortion. A suitable apparatus 29 is provided for this purpose.

The curved mirror 10 fulfills two purposes: On the one hand it focuses ultrasound waves passing through the object 2 at the ultrasonic receiving transducer 22, thereby forming an acoustic image field which generates an image of the object plane 20 on the surface of the receiving transducer 22. On the other hand, due to its oscillations, the mirror 10 scans or sweeps the image of the focal plane 20 in the object 2 across the receiving area of the transducer 22. For this double function, only a single curved mirror 10 is required. No lenses are necessary. This keeps the number of acoustic interfaces low and results in the reduction of artifacts in the image due to multiple reverberations in the image forming apparatus, as mentioned above. The mirror 10 represents a very compact imaging and scanning device.

The entire acoustical path from the wave-generating transducer 6 to the object 2 and from the object 2 via the mirror 10 to the receiving transducer 22 may be filled with a suitable ultrasound guiding medium or liquid such as water. If the entire system is water-filled, and receiving is with a receive array 22 containing a number of elements, then off-axis aberrations near the ends of the receive array 22 may be observed. It is possible, however, to reduce these aberrations, as will be apparent later from the embodiments shown in FIGS. 3 and 4.

Figure 2:
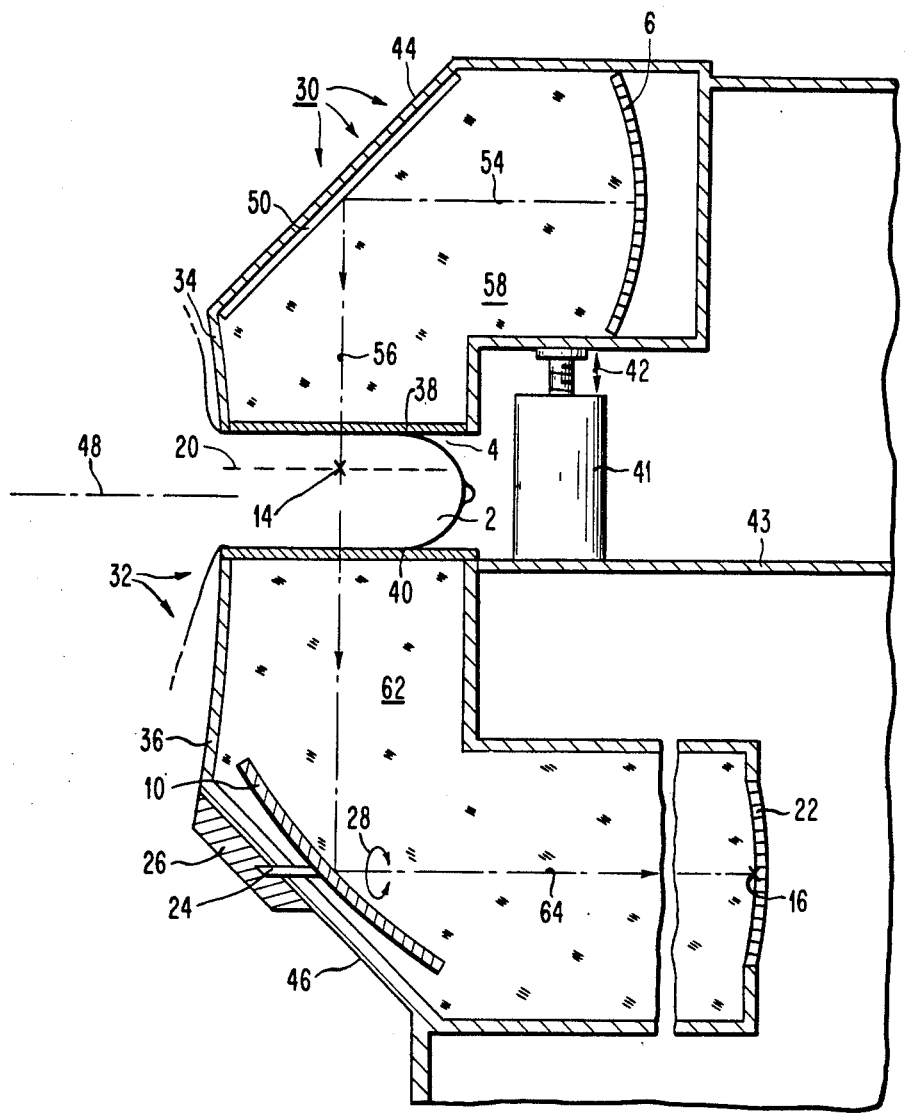
FIG. 2 is a cross-sectional view of an embodiment of an ultrasonic transmission imaging system including a compact scanning device for ultrasound according to this invention, said scanning device containing a curved mirror and a driving mechanism for vibrating the mirror.

With reference to FIG. 2, a patient is sitting upright in front of the ultrasonic transmission imaging system or ultrasound examination apparatus 30. In particular, this apparatus is a breast screening C-scan ultrasonic camera for tumor detection and can be used for routine examinations. The ultrasound apparatus 30 comprises a front portion 32 and a back portion (not shown) which is supported by a pedestal. The front portion 32 supports on its front side two protruding housing compartments 34 and 36. Both compartments 34 and 36 are provided for housing components and parts for generating, transmitting and/or receiving ultrasound waves. Compartment 34 houses a transmitting unit, and compartment 36 houses a receiving unit. The sides of these compartments 34 and 36 that face each other are provided with ultrasonically transparent windows 38 and 40, respectively, forming a free space or an examination gap 4 therebetween. Well-known window materials are, for instance, polystyrene or acrylic plastic.

As illustrated in FIG. 2, the patient's breast 2 is positioned in the examination gap 4 between the ultrasound windows 38 and 40. Ultrasound waves are applied in a vertical direction. The upper compartment 34 is vertically adjustable so as to provide gentle compression to the organ 2 of the patient. Thus the breast 2 is slightly flattened to provide upper and lower substantially parallel surfaces. It has been found that good examination results can be achieved if all parts of the organ 2 under examination have approximately the same thickness. The possibility of adjusting the examination space 4 by any suitable device 41 is indicated in FIG. 2 by a double arrow 42. The device 41 moves one window 38 or 40 toward or away from the other window 40 or 38, respectively. A pneumatic or hydraulic device containing a cylinder and a threaded bar may be used for performing such movement. One of these elements may rest on a support plate 43 attached to the window 40, and the other element may press against a wall element connected to the other window 38. Also other driving means may be applied, such as an electric motor in combination with a gear mechanism and/or a lead screw and/or a lever system (excenter).

As can be seen in FIG. 2, the upper compartment 34 has a sloping upper end face 44, and the lower compartment 36 has a sloping lower end face 46. These sloping end faces 44 and 46 leave free space for the patient's upper and lower body portions.

The front portion 32 of the ultrasound apparatus 30 may be pivoted about a horizontal axis 48 by any well-known means (not shown). Rotation about the horizontal axis 48 passing preferably through the examination gap 4 makes possible examinations of the breast 2 in various directions, e.g. horizontally and vertically.

The transmitting compartment 34 contains an ultrasonic wave generating transducer 6 for providing ultrasonic waves. A transducer 6 which contains a curved array of transmitting transducer elements is well known in the art. The transmitting compartment 34 also contains a flat mirror 50 for deflecting ultrasonic waves emitted from the transducer 6 towards the first ultrasound window 38. The ultrasonic mirror 50 may be positioned at an angle of 45° with respect to the horizontal main axis 54 of the ultrasonic waves. Thus, it can provide for a deflection by 90°. The main axis 56 would now be positioned in a plane vertical to the axis 54. The first ultrasound window 38 contains an ultrasonically transparent rigid plate. The interior of the transmitting compartment 34 is filled with a matching fluid medium 58 such as water.

The first window 38 and the second window 40 define the examination gap 4 for introducing and insonifying the patient's breast 2. The second window 40 is also an ultrasonically transparent rigid plate. The smooth planar surfaces of the first and second windows 38 and 40 compress the breast 2 to an even thickness.

The interior of the receiving compartment 36 is filled with a tissue-velocity matching liquid 62, as water for instance. Contained in the compartment 36 is a curved mirror 10. It is connected to a rocking or sweeping device 26 outside the compartment 36. The rotatable mirror 10 represents a focusing and deflecting unit. In the present embodiment it provides for a deflection by approximately 90°. The main axis 64 is now horizontal again. The unit 10, 24, 26 is used to sweep ultrasonic waves received from the second window 40 across the receiving transducer array 22 arranged within and at the rear of the chamber 36. The receiving transducer array 22 preferably is a well-known curved array of elongated piezoelectric detector elements.

It will be noted that the mirror 10 has again an ellipsoidal reflecting surface which is a portion of an ellipsoid having a first and a second focus 14 and 16, respectively. The first focus 14 defines the plane 20 of interest, and the receiving transducer 22 is positioned in the second focus 16.

It has been pointed out that a curved vibrating or rocking mirror 10 is used as the sweeping device for deflecting the ultrasonic waves. In its resting position, the middle portion of the rocking mirror 10 is arranged at a suitable angle which may be between 30° and 60° (such as 45°) with respect to the main axis 56 of the ultrasound waves received from the second window 40. Thus, it provides for a folding of the ultrasonic path e.g. by 90°. When the mirror 10 is rotationally vibrated about its horizontal axis 24, it will sweep the ultrasound waves across the receiving transducer array 16 at the rear of the water-filled chamber 36. The illustrated apparatus 30 makes use of folding the acoustic main axis twice. Therefore, the instrument's bulk in regions close to the breast 2 of the patient can be kept small.

Figures 3, 4:
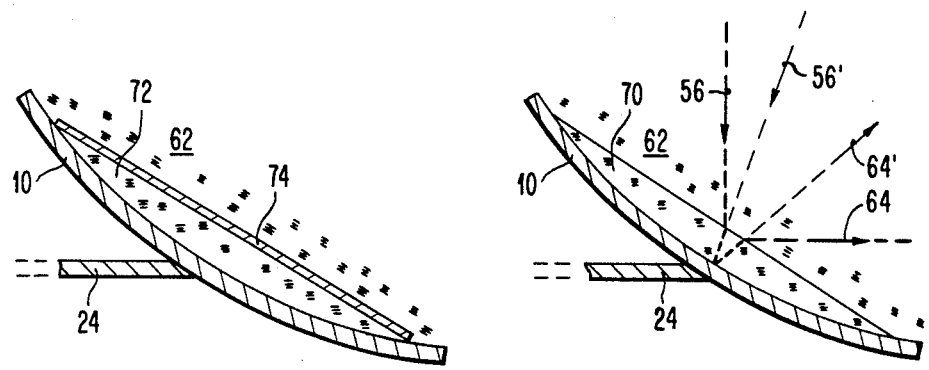
FIG. 3 is a cross-sectional view of another scanning device according to this invention, said scanning device containing a curved mirror covered with a solid substance.
FIG. 4 is a cross-sectional view of still another ultrasound scanning device according to this invention, said scanning device containing a curved mirror filled with a liquid.

In FIGS. 3 and 4 is illustrated that the mirror 10 may be filled with a material or substance 70 and 72, respectively, having a low ultrasound propagation velocity as compared to the liquid 62. As a result, the dimensions of the ellipsoid 12 (see FIG. 1) are increased. This increase is proportional to the difference in index of refraction between the liquid 62 and the material 70 or 72. The reason for such an increase can be seen in FIG. 3. To the mirror 10, the ultrasound waves seem to impinge along a direction 56' and to be reflected along a direction 64'. This will result in an apparatus first focus (not shown) and an apparent second focus (not shown) located along apparent axes 56' and 64'.

In FIG. 3 is illustrated that the substance 70 may be a solid, lining the concave reflecting surface of the mirror 10. And in FIG. 4 is illustrated that the substance 72 may be a liquid filling the space on the surface of the mirror 10. The substance 72 is held in place by a membrane or plate 74. This plate 74 is acoustically transparent. It is comparatively rigid. In particular, the substance 72 may be a fluorinated hydrocarbon. Such a substance is FC-75, produced by 3M Co., U.S.A. If one considers the 2.5:1 ratio of velocities between water (as fluid 62) and FC-75 (as substance 72), it will be apparent that a substantial increase of the magnitude of the ellipsoid 12 (see FIG. 1) will result. Because the mirror 10 is filled, the interface between fluid 62 and low velocity material 70, 72 acts as a lens, making the required mirror 10 flatter and the off-axis angle of operation smaller as compared to that angle where only a liquid 62 such as water is used.

Even further improved results can be achieved if a high velocity fluid 62 is used instead of water.

Due to the substance 70, 72, the ellipsoidal configuration required for the mirror 10 approaches a spherical configuration. In other words, the mirror surface may be formed as a spherical surface.

Due to the aforementioned magnifying effect, which is based on different indices of refraction, only small deflections of the unit 10, 24, 26 and 70 or 72 are required. This again leads to a very compact system.

If the slow velocity material 70 is a solid, then only one surface can cause spurious reflections, namely the surface between the fluid 62 and the slow velocity material 70. By working at angles other than 45°, the reflections can be caused to miss the receiving array 22.

If the slow velocity material 72 is a liquid such as FC-75, then a rigid membrane or a solid sheet 74 must be used to hold the liquid against the surface of the mirror 10. Since the solid sheet 74 has two surfaces, two spurious reflections may occur as well as multiple back and forth reflections between these surfaces. Reflections of this kind could cause problems if received by the receiving array 22. However, also in this case, a non-45°-configuration will suffice to remove resulting artifacts.

Figure 5:
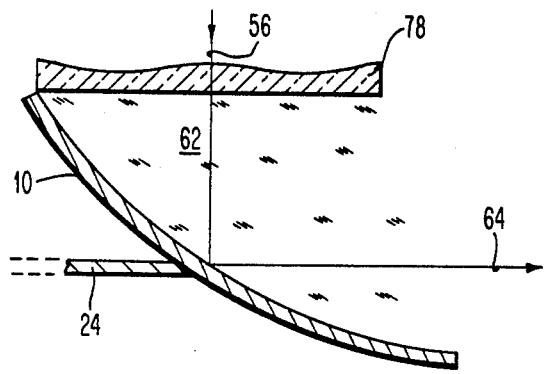
FIG. 5 is a scanning device having a correcting plate positioned in the path before the curved mirror.
Figure 6:
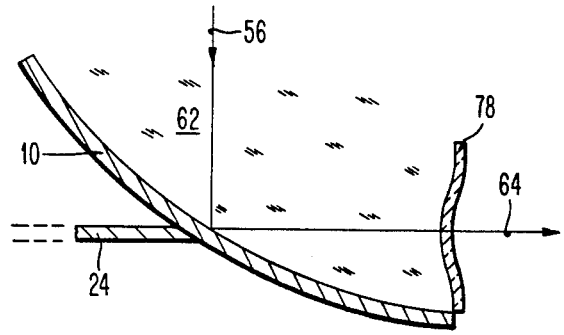
FIG. 6 is a scanning device having a correcting plate positioned in the path behind the curved mirror.
Figure 7:
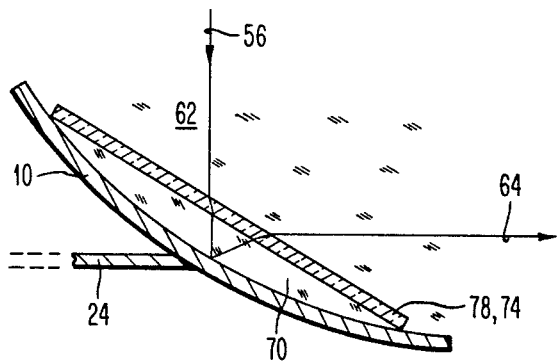
FIG. 7 is a scanning device wherein a sheet holding a substance against the mirror surface is formed as a correcting plate.

A further enhancement may be achieved by a using corrector lens or correction plate 78 as is applied in several kinds of optical mirror telescopes. This correction plate 78 may be placed between the ultrasonic wave generator 6 and the scanning mirror 10, as shown in FIG. 5. It may also be placed between the scanning mirror 10 and the receiving array 22, as shown in FIG. 6. The correction plate 78 may also be formed as the rigid sheet 74 which holds the substance 72 in place, as is shown in FIG. 7. This correction plate 78 works closely together with the scanning mirror 10 to produce improved image quality by correcting the aberrations inherent in the ellipsoidal scanning mirror 10. Such a correction lens 78 gives the designer additional degrees of freedom for designing a system of reduced aberration. It will be noted that the correction plates 78 illustrated in FIGS. 5-7 have different shapes.

The present invention combines convenience in coupling ultrasonic waves to a patient when, for example, imaging the breast, and provides a simple device for scanning.

Since a rocking mirror 10 is utilized to scan the image, there is acheived a considerable design simplicity, few spurious reverberations and convenience in allowing room for a seated patient to be in close proximity to the apparatus.

For breast imaging, the present apparatus design insures imaging close to the chest wall and provides compression of the breast for enhanced image quality. The apparatus is particularly suitable for breast screening, for instance, on a routine basis, and other applications in which a series of images must be produced quickly, and without time consuming preparations.

While the forms of the ultrasonic apparatus for medical examination herein described constitute preferred embodiments of the invention, it is to be understood that the invention is not limited to these precise forms of assembly, and that a variety of changes may be made therein without departing from the scope of the invention.

What is claimed is:

1. An ultrasound apparatus for medical examinations of a patient, comprising in combination:
   (a) an ultrasonic wave-generating transducer for providing ultrasonic waves;
   (b) a first ultrasound window;
   (c) first guiding means containing a fluid medium for guiding said ultrasonic waves to said first ultrasound window;
   (d) a second ultrasound window;
   (e) said first and said second ultrasound windows defining an examination gap for introducing and insonifying a portion of a patient positioned therein, said gap having a main insonification direction;
   (f) an ultrasonic receiving transducer for converting at least a portion of an acoustic image field received from said gap into electrical signals;
   (g) second guiding means containing a fluid medium for guiding ultrasound transmitted through said gap from said second ultrasound window to said ultrasound receiving transducer;
   (h) mirror means associated with said second guiding means and having a curved surface for focusing ultrasound waves passing through said gap at said ultrasonic receiving transducer, thereby forming said acoustic image field and forming an image of said organ of the patient on said receiving transducer; and
   (i) means for oscillating said curved mirror means, said curved mirror means thereby sweeping said acoustic image field across said receiving transducer;

wherein said mirror means comprise a single concave mirror, having an ellipsoidal surface for reflecting said ultrasound waves passing through said gap, and wherein said ellipsoidal surface is a portion of an ellipsoid having a first and a second focus, and wherein said mirror is positioned such that said first focus is located within said gap and said second focus is located on said ultrasonic receiving transducer.

2. The ultrasound apparatus according to claim 1, wherein said second guiding means comprises a fluid of comparatively high ultrasound velocity.

3. The ultrasound apparatus according to claim 2, wherein said fluid is water.

4. The ultrasound apparatus according to claim 3, wherein said curved surface of said mirror is covered with a substance having a velocity of ultrasound which is smaller than that of water.

5. The ultrasound apparatus according to claim 1, wherein said oscillating means comprises:
   (a) a rod having one end attached to said mirror; and
   (b) means for rocking said rod about its longitudinal axis.

6. The ultrasound apparatus according to claim 5, wherein said rocking means comprises an eccentric driven by an electric motor.

7. The ultrasound apparatus according to claim 1, wherein said first and second windows comprise rigid ultrasound transmitting plates for engaging a portion of the patient.

8. The ultrasound apparatus according to claim 1 further comprising means for oscillating said ultrasound receiving transducer in synchrony with said curved mirror means.

9. The ultrasound apparatus according to claim 1, wherein a corrector lens is provided between said wave-generating transducer and said curved surface of said mirror.

10. The ultrasound apparatus according to claim 1, wherein a corrector lens is provided between said curved surface of said mirror means and said ultrasonic receiving transducer.

11. The ultrasound apparatus according to claim 1 wherein a material of relatively low ultrasound velocity is provided in contact with said mirror means, and wherein said material is hold in place by a sheet which is formed as a corrector lens.

12. An ultrasound apparatus for medical examinations of a patient, comprising in combination:
   (a) an ultrasonic wave-generating transducer for providing ultrasonic waves;
   (b) a first ultrasound window;
   (c) first guiding means containing a fluid medium for guiding said ultrasonic waves to said first ultrasound window;
   (d) a second ultrasound window;
   (e) said first and said second ultrasound windows defining an examination gap for introducing and insonifying a portion of a patient positioned therein, said gap having a main insonification direction;
   (f) an ultrasonic receiving transducer for converting at least a portion of an acoustic image field received from said gap into electrical signals;
   (g) second guiding means containing a fluid medium for guiding ultrasound transmitted through said gap from said second ultrasound window to said ultrasound receiving transducer;

(h) mirror means associated with said second guiding means and having a curved surface for focusing ultrasound waves passing through said gap at said ultrasonic receiving transducer, thereby forming said acoustic image field and forming an image of said organ of the patient on said receiving transducer; and (i) means for oscillating said curved mirror means, said curved mirror means thereby sweeping said acoustic image field across said receiving transducer;

wherein said mirror means comprise a single concave mirror, said mirror has a surface which is a portion of a sphere.

13. An ultrasound apparatus for medical examinations of a patient, comprising in combination:

(a) an ultrasonic wave-generating transducer for providing ultrasonic waves;

(b) a first ultrasound window;

(c) first guiding means containing a fluid medium for guiding said ultrasonic waves to said first ultrasound window;

(d) a second ultrasound window;

(e) said first and said second ultrasound windows defining an examination gap for introducing and insonifying a portion of a patient positioned therein, said gap having a main insonification direction;

(f) an ultrasonic receiving transducer for converting at least a portion of an acoustic image field received from said gap into electrical signals;

(g) second guiding means containing a fluid medium for guiding ultrasound transmitted through said gap from said second ultrasound window to said ultrasound receiving transducer;

(h) mirror means associated with said second guiding means and having a curved surface for focusing ultrasound waves passing through said gap at said ultrasonic receiving transducer, thereby forming said acoustic image field and forming an image of said organ of the patient on said receiving transducer; and (i) means for oscillating said curved mirror means, said curved mirror means thereby sweeping said acoustic image field across said receiving transducer;

wherein said second guiding means comprises a fluid of comparatively high ultrasound velocity; and wherein said curved surface of said mirror means is covered with a substance having a comparatively low velocity of ultrasound.

14. The ultrasound apparatus according to claim 13, wherein said liquid is a fluorinated hydrocarbon.

15. The ultrasound apparatus according to claim 14, wherein said substance is a solid which lines said surface.

16. An ultrasound apparatus for medical examinations of a patient, comprising in combination:

(a) an ultrasonic wave-generating transducer for providing ultrasonic waves;

(b) a first ultrasound window;

(c) first guiding means containing a fluid medium for guiding said ultrasonic waves to said first ultrasound window;

(d) a second ultrasound window;

(e) said first and said second ultrasound windows defining an examination gap for introducing and insonifying a portion of a patient positioned therein, said gap having a main insonification direction;

(f) an ultrasonic receiving transducer for converting at least a portion of an acoustic image field received from said gap into electrical signals;

(g) second guiding means containing a fluid medium for guiding ultrasound transmitted through said gap from said second ultrasound window to said ultrasound receiving transducer;

(h) mirror means associated with said second guiding means and having a curved surface for focusing ultrasound waves passing through said gap at said ultrasonic receiving transducer, thereby forming said acoustic image field and forming an image of said organ of the patient on said receiving transducer; and (i) means for oscillating said curved mirror means, said curved mirror means thereby sweeping said acoustic image field across said receiving transducer;

wherein said mirror means comprise a single concave mirror; and wherein the middle portion of said mirror is positioned at an angle of approximately 30°-60° with respect to the main axis of said ultrasound waves which are received from said second window when said mirror is in a rest position.

17. An ultrasound apparatus for examinations of an object, comprising in combination:

(a) an ultrasonic wave-generating transducer for insonification of said object;

(b) an ultrasonic receiving transducer for converting an acoustic image field into electrical signals;

(c) a reflector having a curved surface, which surface is a portion of an ellipsoid having a first and a second focus, said object being placed in said first focus and said receiving transducer being placed in said second focus, whereby said reflector receives ultrasound waves from said insonified object and whereby said reflector generates said acoustic image field representing said object on said receiving transducer; and (d) means for oscillating said reflector, said reflector thereby sweeping said acoustic image field across said receiving transducer.

18. The ultrasound apparatus according to claim 17, further comprising a relatively low ultrasound velocity material in contact with said reflector.

19. The ultrasound apparatus according to claim 17, further comprising means for oscillating said receiving transducer in synchrony with said reflector.

20. The ultrasound apparatus according to claim 17, wherein a corrector lens is provided between said wave-generating transducer and said curved surface of said reflector.

21. The ultrasound apparatus according to claim 17, wherein a corrector lens is provided between said curved surface of said reflector and said ultrasonic receiving transducer.

22. The ultrasound apparatus according to claim 17, wherein a material of relatively low ultrasound velocity is provided in contact with said reflector, and wherein said material is hold in plce by a sheet which is formed as a corrector lens.

* * * * *